United States Patent
Rasmussen et al.

(10) Patent No.: US 12,196,735 B2
(45) Date of Patent: Jan. 14, 2025

(54) METHOD AND SYSTEM FOR PROCESSING A PLURALITY OF AVIAN EGGS

(71) Applicant: Moba Group B.V., Barneveld (NL)

(72) Inventors: Niels Tjørnly Rasmussen, Barneveld (NL); Mads Hartmann Dabros, Barneveld (NL); Simon Kyhn Stenfeldt, Barneveld (NL)

(73) Assignee: Moba Group B.V., Barneveld (NL)

( * ) Notice: Subject to any disclaimer, the term of this patent is extended or adjusted under 35 U.S.C. 154(b) by 324 days.

(21) Appl. No.: 17/800,262

(22) PCT Filed: Feb. 19, 2021

(86) PCT No.: PCT/NL2021/050113
§ 371 (c)(1),
(2) Date: Aug. 17, 2022

(87) PCT Pub. No.: WO2021/167460
PCT Pub. Date: Aug. 26, 2021

(65) Prior Publication Data
US 2023/0090101 A1 Mar. 23, 2023

(30) Foreign Application Priority Data
Feb. 21, 2020 (NL) ..................... 2024969

(51) Int. Cl.
*G01N 33/08* (2006.01)
*A01K 43/00* (2006.01)
*G01N 21/359* (2014.01)

(52) U.S. Cl.
CPC ........... *G01N 33/085* (2013.01); *A01K 43/00* (2013.01); *G01N 21/359* (2013.01)

(58) Field of Classification Search
CPC .... G01N 33/08; G01N 33/085; G01N 21/359; A01K 43/04; A01K 43/00
See application file for complete search history.

(56) References Cited

U.S. PATENT DOCUMENTS 4,161,366 A 7/1979 Bol et al.
4,805,778 A * 2/1989 Nambu .................... B07C 5/00
209/3.3
(Continued)

FOREIGN PATENT DOCUMENTS

CN 109154574 A * 1/2019 ............. A01K 43/00
EP 1 221 613 7/2002
(Continued)

OTHER PUBLICATIONS

International Search Report for PCT/NL2021/050113 dated Mar. 30, 2021.
(Continued)

*Primary Examiner* — Abdullahi Nur
(74) *Attorney, Agent, or Firm* — Stephen J. Weyer, Esq.; Stites & Harbison, PLLC

(57) ABSTRACT

Method for processing a plurality of avian eggs, in particular unfertilized eggs, including:—conveying at least a first egg (E1) having a first eggshell color and a second egg (E2) having a second egg shell color along a conveying path, the first egg shell color being different from the second egg shell color;—illuminating the first egg (E1) with an illumination beam (B) of near infrared light, wherein at least part of the light is transmitted through the egg (E1) and is detected by a near infrared light detector (5);—illuminating the second egg (E2) with the illumination beam (B) of near infrared light, wherein at least part of the light is transmitted through the egg (E2) and is detected by the near infrared light detector (5); processing light detection results of the infrared light detector (5) for determining a condition of the shell of each of the eggs (E1, E2); wherein the illuminating of the eggs (E1, E2) and/or the detection of transmitted light is carried out under substantially the same illumination and/or detection conditions, respectively.

20 Claims, 3 Drawing Sheets

(56) References Cited

U.S. PATENT DOCUMENTS

Figure 1:
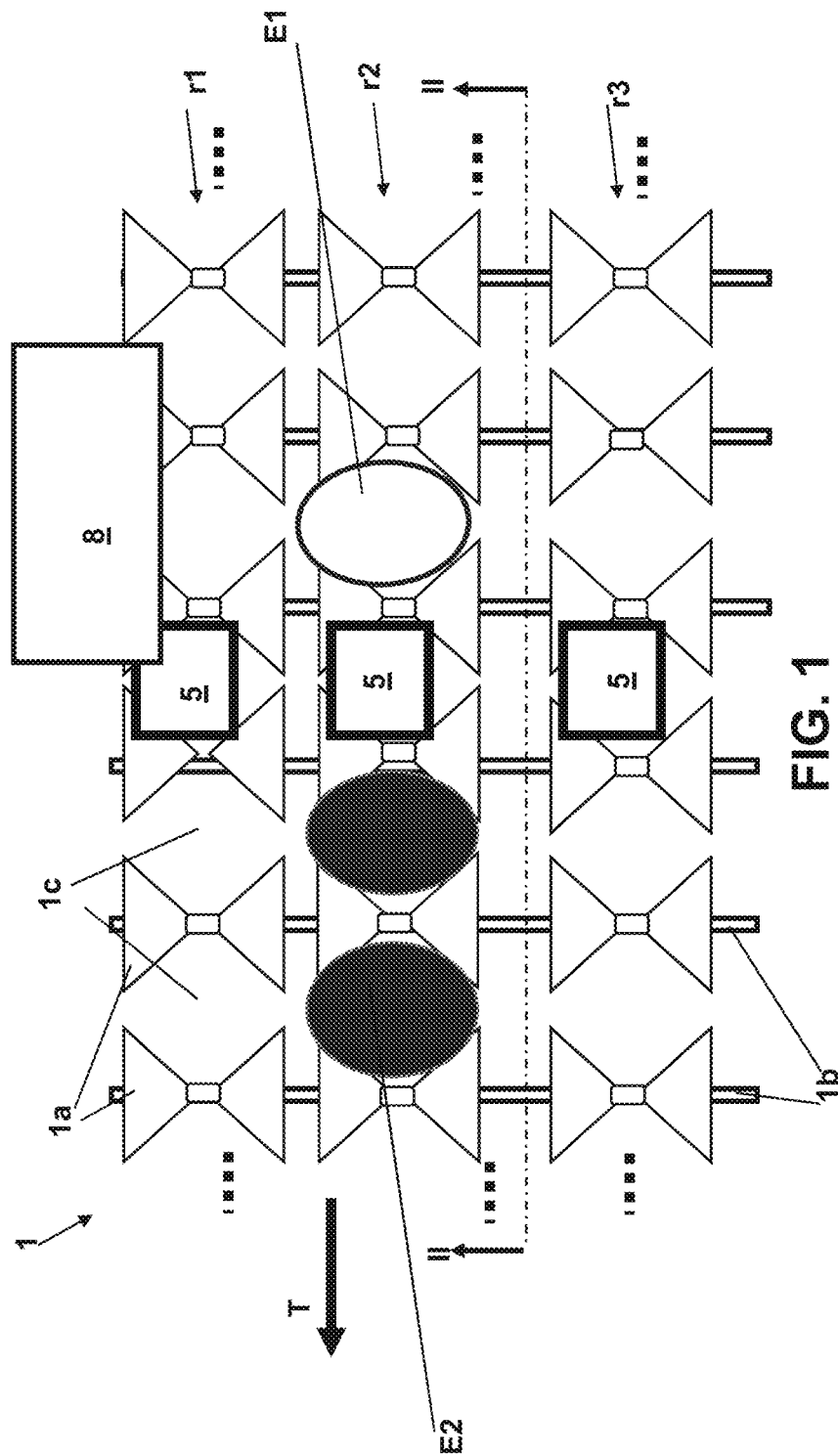

| | | | |
|---|---|---|---|
| 5,615,777 A | 4/1997 | Weichman et al. | |
| 5,900,929 A * | 5/1999 | Hebrank | A01K 45/007 |
| | | | 356/53 |
| 2003/0156273 A1 | 8/2003 | Kageyama et al. | |
| 2019/0041722 A1 | 2/2019 | Walukas et al. | |

FOREIGN PATENT DOCUMENTS

| | | |
|---|---|---|
| JP | 2001021490 | 1/2001 |
| JP | 2017 023126 | 2/2017 |
| WO | WO-2018198923 | 11/2018 |
| WO | WO/2019039319 | 2/2019 |

OTHER PUBLICATIONS

International Preliminary Report on Patentability for PCT/NL2021/050113 dated May 13, 2022.
Notice of Reasons for Refusal dated Sep. 6, 2024 in corresponding Japanese Application No. 2022-549240.

* cited by examiner

METHOD AND SYSTEM FOR PROCESSING A PLURALITY OF AVIAN EGGS

The invention relates to a method and system for processing a plurality of avian eggs, for example poultry eggs, in particular unfertilized eggs.

Egg detection systems are known and marketed by the applicant. An example is the MOBA egg inspector (see www.moba.com), which includes camera's and special lighting, as well as software, for detecting leaking- and dirty eggs on the infeed of egg graders.

Also known are egg processing systems and methods for detecting cracks in eggshells. One method uses acoustic crack detection, wherein the shell is physically disturbed (e.g. by a bouncer) and a resulting sound signal is detected and processed to obtain egg shell structure information.

Yet another known method uses optical egg inspection, see for example WO2019039319 which discloses an egg inspection device having a holding member for holding an egg, irradiation parts for irradiating the egg light, image capturing parts for capturing an image of the egg irradiated with the light, and a determination part for determining surface conditions of the egg. According to the document, near-infrared (NIR) light can be used for illuminating the egg. However, WO'319 states that eggshell color can influence light transmission, resulting in poor contrast.

Optical inspection is also known from e.g. U.S. Pat. No. 5,615,777, which discloses an apparatus for detecting flaws in eggs and for distinguishing between flaws in different natures, the apparatus comprising:
a) means to rotate the egg about its longitudinal axis;
b) means to form at least one laser beam and focus it to a spot focus;
c) means to vibrate the laser beam at a speed and amplitude such that the spot focus appears as a geometric figure selected from closed curves and straight lines;
d) means to direct the at least one laser beam to scan the egg along at least one circumferential path thereabout during at least one revolution of the egg with said at least one vibrating laser beam such that sequential geometric figures of the laser beam overlap one another along the circumferential path;
e) detection means to detect peaks in intensity in light emanating from the egg;
f) signal processing means to develop a progression of signals corresponding to the number, size and character of said peaks in intensity of said light emanating from the egg; and
g) computer means to process said signals and to deduce, from the number, size and character of the peaks in intensity, the nature of a flaw in the egg.

An advantage of acoustic methods over optical methods is that acoustic methods are not dependent on egg shell color. In particular, eggs having white shells and eggs having brown shells can be processed by the same acoustic testing apparatus to provide reliable crack detection results.

On the other hand, optical inspection methods have the advantage that they can use contactless detection means, providing advantages in view of hygiene and detector cleanliness.

JP2017023126 discloses a device and method for inspecting an egg stored in a container, to easily detect any defects on a surface of the egg such as cracks. According to the document, the respective light source emits infrared rays. According to JP'126, in particular, since infrared rays have the property of passing through the egg white, even if the eggshell cracks and the contents of the egg E leak into the pack, only the cracked part of the eggshell is white in the captured image. Further, the document states that since near-infrared light having a wavelength of 780 nm to 870 nm is used, it is possible to take a suitable image, and that if a wavelength shorter than 780 nm is used, it is easily affected by the eggshell color.

The present invention aims to provide an improved method for processing a plurality of eggs. In particular the invention aims to provide a method that can alleviate above-mentioned problems of known methods. One object is to efficiently process a plurality of differently colored eggs, for example by processing one or a plurality of batches of eggs, in a swift, hygienic manner, wherein eggshell defects, e.g. cracks, can be detected in a reliable, preferably economical manner.

According to an aspect of the invention this is achieved by the features of claim 1.

Advantageously, there is provided an egg processing method including:
conveying at least a first egg having a first eggshell color and a second egg having a second egg shell color along a conveying path, the first egg shell color being different from the second egg shell color;
illuminating the first egg with an illumination beam of near infrared light, wherein at least part of the light is transmitted through the egg and is detected by a near infrared light detector;
illuminating the second egg with the illumination beam of near infrared light, wherein at least part of the light is transmitted through the egg and is detected by the near infrared light detector;
processing light detection results of the infrared light detector for determining a condition of the shell of each of the eggs;
wherein the illuminating of the eggs is carried out under substantially the same illumination conditions (i.e. parameters) and/or wherein the detection of transmitted light is carried out under substantially the same detection conditions (i.e. parameters).

It has been found, surprisingly, that near infrared light can illuminate eggs of mutually different color (e.g. a brown egg having an optically brown shell to the human eye and a white egg having an optically white shell to the human eye), wherein the resulting transmitted light has about the same intensity for the differently colored eggs. In other words: it has been surprisingly found that eggshell color as such does not substantially alter transmission of near infrared light. This means that the detector, detecting transmitted near infrared light, can maintain a certain predetermined light detecting state during detecting light resulting from eggs having mutually different shell color, without hampering detecting results (and subsequent processing results).

For example, the illuminating of the first egg can be carried out under substantially the same illumination conditions/parameters as the illuminating of the second egg. In particular this means that the same near infrared illumination beam is used, at e.g. the same near infrared wavelength(s) and the same beam intensity. As will be clear to the skilled person, this beam intensity or respective beam power can be expressed in Watt/surface area ($W/m^2$), luminous intensity, or the-like. In a further embodiment, the illumination beam includes narrowband light of at least one (preferably only one) predetermined narrowband near infrared light wavelength. In a preferred embodiment, the illumination beam is a light beam of substantially a single wavelength of the NIR spectrum. In an embodiment, the substantially single wavelength can be for example a center wavelength of a narrow-band spectrum part of an LED light emitter (e.g. concerning a respective spectral line of Light Emitting Diode light emission), as will be appreciated by the skilled person.

Also, according to an advantageous aspect, the detector can have the same predetermined detector state during the detecting of the light that has been transmitted by the first egg and the light that has been transmitted by the second egg. In particular, a detector's light sensitivity (in particular light sensitivity for the wavelength of the emitted beam) can remain fixed during the detecting of that light.

More particularly, e.g., the detector can include one or more photo-sensors, configured to generate an electric sensor signal upon detecting of light (which sensor signal can be processed by processing means for determining an eggshell condition). Furthermore, the detector may include optional further optical means, e.g. one or more optical elements, one or more lenses, and/or one or more optical filters, a shutter, for directing and optionally filtering incoming light onto the one or more photo-sensors to be detected thereby. It follows that such detector means (i.e. the one or more photo-sensors and said optional further detector components) preferably have the same respective operating state during the detection of light emanating from the first egg and light emanating from the second egg. Thus, in case of the presence of a variable filter (if any) in the detector, the state of such a filter is the same during detecting of the light emanating from each of the two different eggs. Similarly, any detector sensor power, bias voltage for powering resp. biasing the detector or photo-sensor(s), can also be kept constant.

Summarizing, this means that the detector, detecting transmitted near infrared light, can maintain a certain predetermined light detecting state during detecting light resulting from eggs having mutually different shell color, without hampering detecting results (and subsequent processing results). This leads to improved egg processing, producing reliable results for a mix of differently colored eggs.

Regarding the color of the egg shell, for example, a white egg can have a substantially unpigmented egg shell, whereas the other (nonwhite) egg can have a pigmented eggshell (e.g. including protoporphyrin), as will be appreciated by the skilled person. Also, a nonwhite eggshell can e.g. have a uniform or non-uniform (e.g. speckled) color. A white eggshell can have a uniform white color.

In a further embodiment, the wavelength of the near infrared light of the illumination beam is at least 700 nm and preferably at most 1000 nm, e.g. preferably at most 900 nm, more preferably at most 800 nm, for example a wavelength in the range of 700-800 nm. Good results have been obtained with a wavelength smaller than 750 nm, in particular a wavelength in the range of 720-740 nm (e.g. a wavelength of about 720 nm).

Also, it has been found that by using a wavelength of at most 800 nm (or a wavelength smaller than 800 nm), relatively low costs detecting means can be utilized as near infrared light detector.

Further, an aspect of the invention provides a system for processing a plurality of avian eggs, in particular unfertilized eggs, in particular a system configured for carrying out a method according to the invention, wherein the system includes:

a conveyor, configured for conveying a plurality of eggs along a conveying path, in particular in at least one row;

at least one beam source for emitting an illumination beam of near infrared light towards the egg conveying path, for illuminating the eggs during operation;

at least one light detector, arranged for detecting light emanating from the egg conveying path, in particular light transmitted through the eggs during operation;

processing means configured to process light detection results of the infrared light detector, in particular for determining a condition of the shell of each of the eggs during operation;

characterized in that the system is configured to maintain substantially the same egg illumination conditions and/or detection conditions when eggs having mutually different eggshell colors are being processed thereby.

In this way, above-mentioned advantages can be achieved.

In preferred embodiments, both the illumination conditions (parameters) and detection conditions (parameters) are maintained, but that is not required.

As follows from the above, the beam source is preferably configured to emit the same illumination beam, i.e. of the same intensity/beam power, to the two different eggs during operation. Similarly, it is preferred that the detector is configured to apply the same predetermined detector state during operation, in particular during an operational period in which the different eggs (of mutually different eggshell color) are being conveyed along the source and detector (to be examined).

Further extra advantageous embodiments of the invention are provided in the dependent claims.

Figure 2:
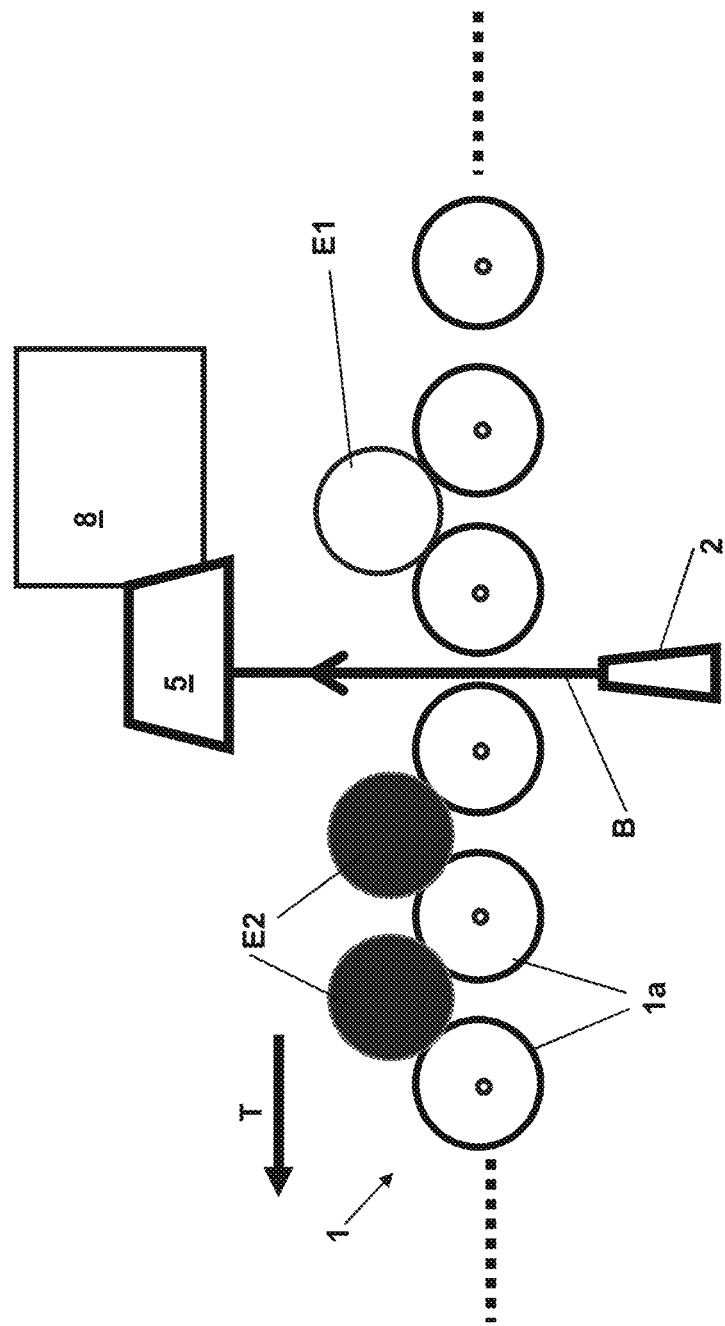

The invention will now be explained in more detail, with reference to the drawing. Therein shows:

FIG. 1 schematically part of a non-limiting example of an egg processing system, in a top view;

FIG. 2 a cross-section over line II-II of FIG. 1; and

Figure 3:
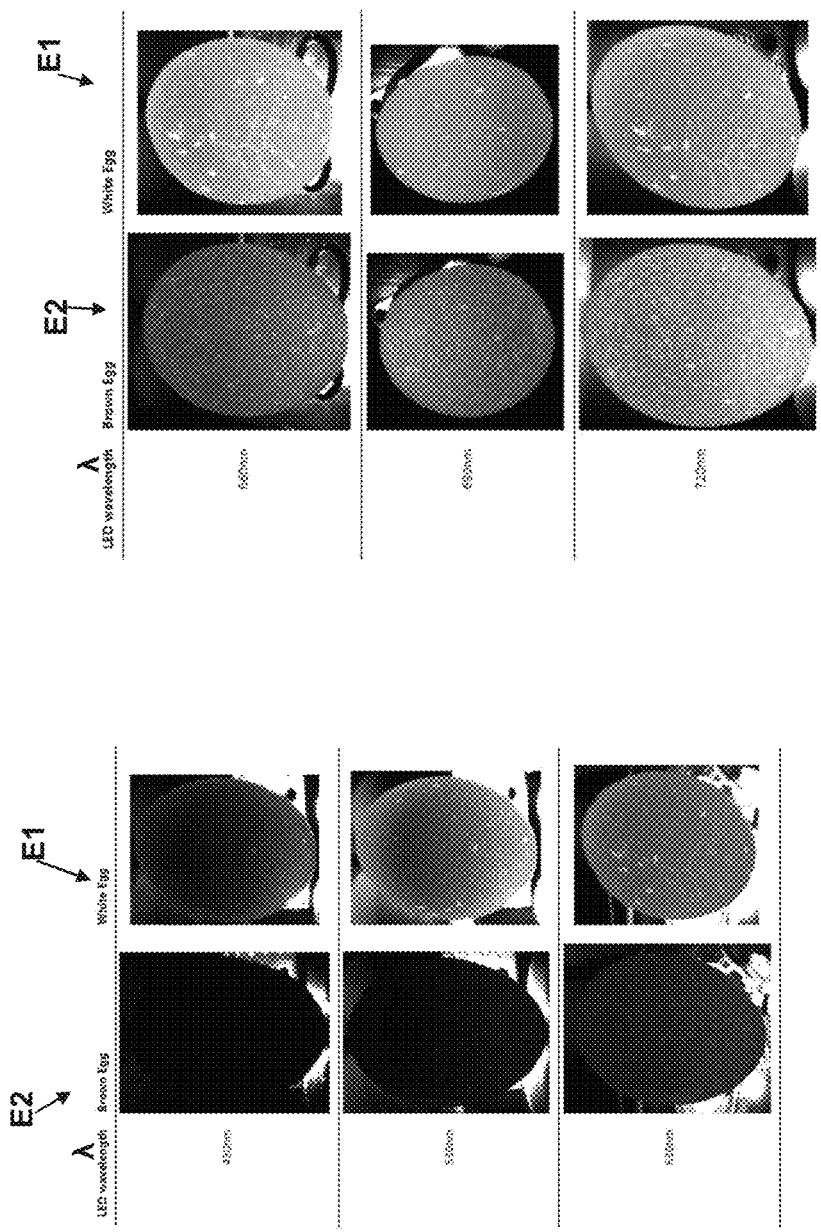

FIG. 3 shows detector results concerning a various beam wavelengths.

FIGS. 1-2 depict an egg processing system, including a conveyor 1 (only part being shown), configured for conveying a plurality of eggs E1, E2 along a conveying path (in a transport direction T), in particular as a number of rows of eggs E1, E2. Three parallel rows r1, r2, r3 are depicted in this example; naturally, the conveyor 1 may be configured to convey the eggs in more or less than three rows.

As is shown in the drawing, during use, the eggs can have different egg shell colors. For example, the drawing shows each first egg E1 having a first eggshell color that is white, wherein eggshell color of each second egg E2 is nonwhite, for example brown. As will be explained in the following, the present system can examine both types of eggs E1, E2 in a straight-forward manner.

Preferably, the conveyor 1 is an endless conveyor, e.g. an endless roller conveyer 1. It can be configured for rotating the eggs during transport, e.g. respective longitudinal egg axes. In particular, the roller conveyor can include egg supporting components, for example parallel diabolo shaped (preferably rotating) rollers 1a, defining nests there-between for receiving (and rotating) the eggs E1, E2. The egg supporting elements (e.g. rollers) 1a can be mounted on respective shafts 1b that can be driven by suitable drive means (e.g. a motor, transmission belts or chains and the-like, not shown) for moving the shafts and rollers in the conveying direction T.

It follows that the conveyor 1 can include or define egg receiving nests 1c that are partly open at respective lower (egg supporting) sides, allowing light transmission along respective egg supporting elements (in this case along rollers) 1a.

The system further includes a number of light beam sources 2 for emitting respective illumination beams B of near infrared light towards the egg conveying path, for illuminating the eggs E1, E2 during operation. In the present example, each NIR light beam source 2 (one being depicted) is arranged at a vertical level below a vertical level of the egg conveying path (see FIG. 2). The present light source 2 is arranged to emit the light beam upwardly, so that passing eggs E1, E2 of a respective row r2 are subsequently illuminated by the beam B (the beam entering respective egg receiving nests via respective open sides of those nests, in this example). The system can include various numbers of light sources 2, wherein each source 2 can be configured to emit one or more beams B e.g. for illuminating passing eggs of one or more conveyor rows r1, r2, r3. In a non-limiting example, the light source includes one or more light emitting diodes (LEDs) for emitting the beam B.

Preferably, each light source 2 is configured to emit or provide a collimated or focused beam B, in particular illuminating a only part of an outer surface of each egg shell of a passing egg (E1, E2).

A wavelength of the near infrared light of the illumination beam B, generated by the source 2, can be at least 700 nm and preferably at most 1000 nm, for example a wavelength in the range of 700-800 nm, and preferably a wavelength smaller than 750 nm, in particular a wavelength of about 720 nm. The wavelength of the near infrared light is most preferably in the range of 710-750 nm, preferably the range of 720-740 nm.

Also, preferably, the system is configured such (e.g. a conveyor transport speed and egg rotation speed is set such) that during operation, each egg E1, E2 rotates about a respective longitudinal egg axis over when it is being illuminated by the light beam B.

In the drawing (FIG. 2), the beam source 2 is depicted as emitting the beam towards the detector 5 (see below), but that is not required (in particular in case the eggs internally diffuse received light). The source 2 may operate continuously, but preferably emits the beam intermittently. Also, in an embodiment, operation of the beam source 2 can be synchronized with the conveyor 1 (e.g. with a conveyor speed) such that the source 2 only generates the beam B to illuminate a passing egg, wherein the source does not generate the beam otherwise (e.g. for saving energy and/or to avoid any opposite detector 5 being irradiated directly by the source 2).

Further, the system includes a number of light detectors 5, arranged for detecting light emanating from the egg conveying path, in particular light transmitted through the eggs E1, E2 during operation. In this example, three light detectors 5 are depicted, located at a vertical level above the egg conveyor 1. Thus, contamination of the detectors 5 (e.g. by dirt or other substances that may be present on passing eggs) can be prevented or significantly reduced. Each of these light detectors 5 can be associated with one of the transport rows r1, r2, r3 defined by the conveyor 1, and e.g. with one of said light beam sources 2. Alternatively, for example, a single detector 5 can be installed for detecting light emanating from eggs of several of the rows r1, r2, r3. Besides, alternatively, one or more detectors 5 can be located at another level, e.g. at or below a level of egg transport, and/or at different locations.

Each detector 5 can e.g. be configured to generate a detection signal, for example a digital image of the egg. In an embodiment, the respective detector signal or image can encompass the entire contour of the egg (see FIG. 3).

Further, the system includes processing means 8 (drawn schematically) configured to process light detection results of the infrared light detector 5, in particular for determining a condition of the shell of each of the eggs E1, E2 during operation. The processing means 8 can be configured in various ways, and can include e.g. processor software, processor hardware, a computer, data processing means, a memory for storing data to be processed, et cetera. Also, the processor means 8 can include or be connected to various respective communication means for allowing communication with the light detectors 5 for receiving detection results thereof, or the processing means 8 and detector(s) 5 can be integrated with each other. Besides, the processing means 8 can include e.g. a user interface for allowing operator interaction with the central processor, and e.g. for outputting data processed by the processor.

The processing means 8 are preferably configured to process light detection results for detecting any eggshell cracks of the eggs E1, E2. This processing as such can be carried out in various ways, as will be appreciated by the skilled person. For example, the processing means 8 can be configured to compare detection results with predetermined threshold data or calibration data, that may be stored in the processing means 8 or otherwise available to the processing means. For example, the processing means 8 can be configured to classify an examined egg as being 'good' (uncracked) in case it follows from the comparison that a respective detection signal is below a predetermine threshold, or in case a respective detection image substantially matches egg calibration image data of uncracked egg shells. Similarly, the processing means 8 can be configured to classify an examined egg as being 'bad' (cracked) in case it follows from the comparison that the respective detection signal is above a predetermine threshold, or in case a respective detection image substantially matches one or more calibration data images concerning cracked egg shells. Besides, the system can be configured to reject eggs that have been classified 'bad' (cracked) by the processing means, e.g. via egg removal means (not shown) for removing such eggs from the conveying path.

In a non-limiting example, respective image processing means can include a neural network, that can be based e.g. on machine learning from earlier calibration detection results (utilizing the detector 5 and beam source 2) on one hand and human (visual) inspection on the other, of a plurality of eggs including eggs of different color wherein part of the plurality of eggs contain eggshell cracks (or other physical shell irregularities).

In the present example, the processing means can apply a signal processing method that remains the same (i.e. processing parameters do not have to be altered) for processing detector detection signals (e.g. generated images) concerning first eggs E1 and second eggs E2. Thus, signal processing can be achieved in a straight-forward manner.

As is mentioned above, the system is preferably configured to maintain substantially the same egg illumination conditions/parameters when eggs E1, E2 having mutually different eggshell colors are being processed thereby. In particular, the same illumination beam B (having the same or constant beam intensity and the same spectrum) is generated by the source, for illuminating first eggs E1 and second eggs E2. Also, preferably, the respective detector 5 is preferably not adjusted during its operation (independent of whether the detector 5 is detecting light transmitted via a first egg or via a second egg) to detect light emanating from the plurality of eggs E1, E2 (of the same, respective passing row r1, r2, r3).

During operation the system carries out a method for processing a plurality of eggs E1, E2, in particular unfertilized (e.g. poultry) eggs.

The eggs can be supplied, i.e. fed to the conveyor 1, in various ways, for example via a non-depicted upstream egg supplier.

The conveyor 1 conveys the eggs E1, E2 along respective transport paths, in particular by holding the eggs in respective conveyor nests 1c. During use, first eggs E1 (having the first eggshell color) and the second eggs E2 (having the second egg shell color) are conveyed along the conveying path. The first egg shell color significantly differs from the second egg shell color.

All eggs E1, E2 are illuminated. In particular, this involves illuminating each first egg E1 with the illumination beam B. At least part of the light that is received by the egg E1, is transmitted through the egg E1 (i.e. at least part of the light entering the egg via the shell, to be diffused or scattered by contents of the egg E1, to be at least partly emitted via the eggshell out of the egg again), and is detected by the near infrared light detector 5 (for example by taking one or more digital images of the egg). Also, each second egg E2 is illuminated, with the illumination beam B, wherein at least part of the light is transmitted through each second egg E2 (i.e. at least part of the light entering the egg via the shell, to be diffused or scattered by contents of the egg E2, to be at least partly emitted via the eggshell out of the egg again), is detected by the near infrared light detector (again, for example, by taking one or more images of the egg). As follows from FIG. 1, the row of eggs can pass the source 2 and detector 5 so that the respective eggs E1, E2 can be illuminated (and detected/imaged) in sequence, one after the other.

Preferably, as is mentioned before, the illumination beam can be collimated or focused beam, in particular illuminating a only part of an outer surface of each egg shell of a passing egg (E1, E2).

For example, as in this embodiment, the illumination beam B of near infrared light is passed along a predetermined beam path, wherein each of the first and second egg E1, E2 is conveyed through the same beam path of the illumination beam, to be illuminated thereby.

The illuminating of the eggs E1, E2 is carried out under substantially the same illumination parameters. In particular, to this aim, a beam intensity (W/m$^2$) of the illumination beam B remains substantially the same for each egg illumination. Also, the wavelength (or spectrum) of the beam remains the same.

In this example, the detector 5 has the same respective operating state (e.g. the same light sensitivity) during the detection of light emanating from the first egg E1 and light emanating from the second egg E2. Thus, in case of the presence of a variable filter (if any) in the detector, the state of such a filter is the same during detecting of the light emanating from each of the two different eggs. Similarly, any detector sensor power, bias voltage for powering resp. biasing the detector or photo-sensor(s), can also be kept constant. Similarly, e.g. a shutter speed of a detector shutter (if available) can remain the same.

Next, after light detection, the processing means 8 can process the light detection results (e.g. images) received from respective near infrared light detector 5, for determining a condition of the shell of each of the eggs E1, E2. The processing on each of received data/images is preferably carried out in the same manner, e.g. by the same algorithm or image processing method, irrespective of egg shell color relating to the detected/imaged eggs.

The light detection results can be processed for detecting eggshell cracks, wherein an egg having a detected crack is preferably removed from a conveying path.

Thus, a large number of eggs can be inspected, using substantially the same system components 2, 5, 8 without having to adjust operating parameters in case eggs of different shell colors are fed (in)to the system.

The presently depicted example in particular concerns system operation that can include inspecting a single batch of eggs, the batch including a mix of first eggs E1 and second eggs E2, for example a random mix viewed along a conveying direction T.

In another embodiment, the method can include subsequently inspecting a batch of first eggs E1 (the first batch not including second eggs E2) and a batch of second eggs E2 (without any first eggs E1), wherein preferably each egg of each of the batches is illuminated by an or the illumination beam B under substantially the same illumination conditions/parameters and is preferably also examined using substantially the same detection conditions. Thus, also, as above, operating parameters of other system components such as detector(s) and processing means 8 can remain the same.

Thus, also, different batches can be processed sequentially by the system, without having to alter or adjust detector(s) 5, and using the same signal processing (e.g. the same data processing method) by the processing means 8 without adjusting processing parameters.

FIG. 3 shows detector results concerning illuminating white eggs and brown eggs, at different wavelengths $\lambda$ (in the range of 430-720 nm). The images have been made with a monochrome camera (sensitive to a broad spectrum that includes these wavelengths). It follows that the brown egg does not transmit low wavelength light (contrary to the white egg), but that, surprisingly, light of $\lambda$=720 nm is transmitted substantially equally by the brown and white egg.

It is self-evident that the invention is not limited to the above-described exemplary embodiments. Various modifications are possible within the framework of the invention as set forth in the appended claims.

In this application, the eggs to be processed are in particular non-living, dead eggs, i.e. eggs for consumption that are not fertilized (and do not contain any embryo). The avian/bird eggs can be poultry eggs, for example chicken eggs.

Also, in a preferred embodiment, the detector, detecting transmitted near infrared light, maintains a certain predetermined light detecting state during detecting light resulting from eggs having mutually different shell color, without hampering detecting results (and subsequent processing results). However, that is not essential. Alternatively, for example, at least part of the detector may change a respective state with respect of detecting light emanating from various (e.g. different) eggs.

Also, it will be clear that each detector can be located at various locations, and can be configured e.g. to detect light that has been transmitted from a single egg or light that has been transmitted from a plurality of eggs. For example, the system can include a plurality of detectors for viewing an egg from different viewing directions. For example, at least one camera-type detector can be provided, each camera being arranged for taking images of one or more eggs, to be examined, at the same time.

Furthermore, each said NIR light source can be arranged at various positions, for example below, at and/or above a vertical level of the egg(s). Moreover, a plurality of light sources can be implemented for illuminating (e.g. simultaneously) illuminating a single egg E1, E2, from the same or from different directions.

Also, for example, the color of the eggshell can be the color as perceived by the naked (human) eye as will be appreciated by the skilled person.

The invention claimed is:

1. A method for processing a plurality of avian eggs, said method comprising:
   conveying at least a first egg having a first eggshell color and a second egg having a second egg shell color along a conveying path, the first egg shell color being different from the second egg shell color;
   illuminating the first egg with an illumination beam of near infrared light, wherein at least part of the light is transmitted through the egg and is detected by a near infrared light detector;
   illuminating the second egg with the illumination beam of near infrared light, wherein at least part of the light is transmitted through the egg and is detected by the near infrared light detector; and
   processing light detection results of the infrared light detector for determining a condition of the shell of each of the eggs;
   wherein the illuminating of the eggs and/or the detection of transmitted light is carried out under substantially the same illumination and/or detection conditions respectively.

2. The method according to claim 1, wherein a wavelength of the near infrared light of the illumination beam is smaller than 800 nm.

3. The method according to claim 1, wherein the wavelength of the near infrared light of the illumination beam is in the range of 710-750 nm.

4. The method according to claim 1, wherein an illumination beam of near infrared light is passed along a predetermined beam path, wherein each of the first and second egg is conveyed through the same beam path of the illumination beam, to be illuminated thereby.

5. The method according to claim 1, wherein a beam intensity of the illumination beam remains the same for each egg illumination, wherein in particular the intensity of the illumination beam during illumination of the first egg is the same as the intensity of the illumination beam during illumination of the second egg.

6. The method according to claim 1, wherein a wavelength of the near infrared light of the illumination beam is at least 700 nm.

7. The method according to claim 1, wherein the first eggshell color is white, and wherein the second eggshell color is nonwhite.

8. The method according to claim 1, wherein the illumination beam is a collimated or focused beam.

9. The method according to claim 1, wherein the light detection results are processed for detecting eggshell cracks.

10. The method according to claim 1, including subsequently inspecting a batch of first eggs and a batch of second eggs, wherein each egg of each of the batches is illuminated by an or the illumination beam under substantially the same illumination conditions and/or is examined using substantially the same detection conditions.

11. The method according to claim 1, including inspecting a single batch of eggs, the batch including a mix of first eggs and second eggs.

12. A system for processing a plurality of avian eggs, said system comprising:
    a conveyor, configured for conveying a plurality of eggs along a conveying path;
    at least one beam source for emitting an illumination beam of near infrared light towards the egg conveying path, for illuminating the eggs during operation;
    at least one light detector, arranged for detecting light emanating from the egg conveying path, in particular light transmitted through the eggs during operation; and
    processing means configured to process light detection results of the infrared light detector, in particular for determining a condition of the shell of each of the eggs during operation, wherein the system is configured to maintain substantially the same egg illumination conditions and/or detection conditions when eggs having mutually different eggshell colors are being processed thereby.

13. The system according to claim 12, wherein a wavelength of the near infrared light of the illumination beam is at least 700 nm.

14. The system according to claim 13, wherein the wavelength of the near infrared light is in the range of 710-750 nm.

15. The system according to claim 12, wherein the processing means are configured to process light detection results for detecting any eggshell cracks of the eggs.

16. The system according to claim 12, including at least one roller conveyer for conveying the eggs in at least one row along a respective conveying path.

17. The system according to claim 12, including a plurality of light beam sources for emitting respective illumination beams.

18. The method according to claim 1, wherein each first egg has a substantially unpigmented egg shell, in particular an egg shell that does not contain protoporphyrin, and whereas each second egg has a substantially pigmented egg shell.

19. The method according to claim 18, wherein each first egg has a uniform white color.

20. The system according claim 12, wherein the processing means include a neural network.

* * * * *